US012557868B2

(12) United States Patent
Reitebuch

(10) Patent No.: US 12,557,868 B2
(45) Date of Patent: Feb. 24, 2026

(54) PROTECTIVE HELMET

(71) Applicant: Schuberth GmbH, Magdeburg (DE)

(72) Inventor: Sebastian Reitebuch, Berlin (DE)

(73) Assignee: Schuberth GmbH, Magdeburg (DE)

( * ) Notice: Subject to any disclaimer, the term of this patent is extended or adjusted under 35 U.S.C. 154(b) by 0 days.

(21) Appl. No.: 18/572,820

(22) PCT Filed: Jun. 29, 2022

(86) PCT No.: PCT/EP2022/067881
§ 371 (c)(1),
(2) Date: Dec. 21, 2023

(87) PCT Pub. No.: WO2023/275136
PCT Pub. Date: Jan. 5, 2023

(65) Prior Publication Data

US 2024/0285019 A1 Aug. 29, 2024

(30) Foreign Application Priority Data

Jun. 29, 2021 (DE) ..................... 10 2021 116 755.8
Jul. 5, 2021 (DE) ..................... 10 2021 117 299.3

(51) Int. Cl.
*A42B 3/32* (2006.01)
*A42B 3/22* (2006.01)
*A61F 9/02* (2006.01)

(52) U.S. Cl.
CPC .............. *A42B 3/326* (2013.01); *A42B 3/223* (2013.01); *A61F 9/029* (2013.01)

(58) Field of Classification Search
CPC .......... A42B 3/326; A42B 3/223; A61F 9/029
(Continued)

(56) References Cited

U.S. PATENT DOCUMENTS 7,814,579 B2 * 10/2010 Dion ...................... A42B 3/326 2/410
9,713,756 B1 * 7/2017 Tran .................. A63B 24/0021
(Continued)

FOREIGN PATENT DOCUMENTS

BR 102022022924 A2 * 5/2024 ............... A42B 3/04
CA 2736646 A1 * 9/2007 ............. A42B 3/125
(Continued)

OTHER PUBLICATIONS

PCT/EP2022/067881 International Search Report mailed Oct. 4, 2022.
CN 202280045460.9 Office Action dated Jan. 19, 2026.

*Primary Examiner* — Lori L Baker
(74) *Attorney, Agent, or Firm* — Wood Herron & Evans LLP

(57) ABSTRACT

A motorcycle helmet, having a helmet shell, a chin part for covering a chin portion of a wearer, and a visor, uses a coupling mechanism by means of which the chin part is fastened to the helmet shell and pivotable between a lower position and an upper position. With the chin part in the lower position, by means of the coupling mechanism, the visor can assume a respective pivoting position between a closed position and an open position. The coupling mechanism is further designed, upon pivoting of the chin part from the upper position into the lower position after the chin part has previously been pivoted from the lower position into the upper position, to cause the visor to occupy a pre-pivoting position differing from the closed position, which pre-pivoting position the visor occupied before the pivoting of the chin part from the lower position into the upper position.

22 Claims, 11 Drawing Sheets

Figure 1:
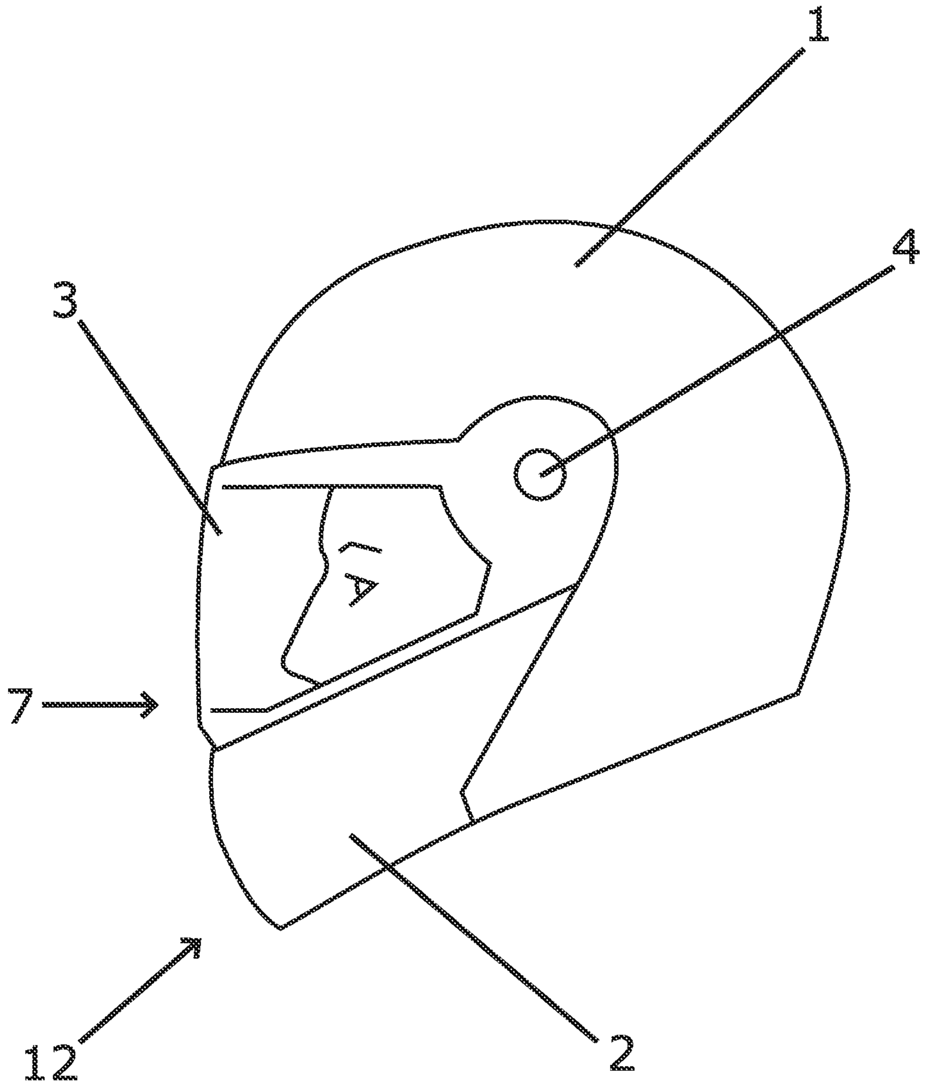

(58) Field of Classification Search
USPC ........................................................ 4/424, 421
See application file for complete search history.

(56) References Cited

U.S. PATENT DOCUMENTS

| | | | | |
|---|---|---|---|---|
| 10,426,665 | B1 * | 10/2019 | Fridie | A61F 9/02 |
| 11,330,858 | B2 | 5/2022 | Nimura | |
| 11,771,163 | B2 * | 10/2023 | Abdollahi | G02B 27/0176 2/422 |
| 12,220,016 | B1 * | 2/2025 | Bologna | A42B 3/227 |
| 2007/0113318 | A1 * | 5/2007 | Weston | A42B 3/281 2/171.3 |
| 2011/0078846 | A1 * | 4/2011 | Gafforio | A42B 3/326 2/424 |
| 2013/0081199 | A1 | 4/2013 | Nimura | |
| 2015/0135416 | A1 * | 5/2015 | Hendl | A42B 3/32 2/424 |
| 2018/0279709 | A1 * | 10/2018 | Durham | A42B 3/223 |
| 2022/0361619 | A1 * | 11/2022 | Weber | A61F 9/029 |
| 2025/0089835 | A1 * | 3/2025 | Hanudel | A42B 3/326 |

FOREIGN PATENT DOCUMENTS

| | | | | | |
|---|---|---|---|---|---|
| CA | 3223365 | A1 | * | 6/2024 | A42B 3/223 |
| CN | 101212913 | A | * | 7/2008 | A42B 3/222 |
| CN | 101991208 | A | * | 3/2011 | A42B 3/326 |
| CN | 101991208 | B | * | 6/2012 | A42B 3/326 |
| CN | 110650643 | B | | 1/2022 | |
| DE | 102014218041 | A1 | * | 3/2016 | A42B 3/326 |
| DE | 102021121600 | B4 | * | 4/2025 | A42B 3/185 |
| EP | 0797935 | A1 | | 10/1997 | |
| EP | 1265506 | A1 | | 12/2002 | |
| EP | 3928651 | A1 | * | 12/2021 | A42B 3/326 |
| EP | 4505894 | A1 | * | 2/2025 | A42B 3/062 |
| ES | 2404171 | A1 | * | 5/2013 | A42B 3/04 |
| GB | 2633558 | A | * | 3/2025 | A42B 3/105 |
| WO | WO-2007122496 | A1 | * | 11/2007 | C07C 67/03 |
| WO | WO-2009095420 | A1 | * | 8/2009 | A42B 3/222 |
| WO | WO-2012047936 | A2 | * | 4/2012 | A42B 3/04 |
| WO | WO-2013093008 | A2 | * | 6/2013 | A42B 3/08 |
| WO | WO-2016090400 | A1 | * | 6/2016 | A42B 3/04 |
| WO | WO-2018099645 | A1 | * | 6/2018 | A42B 3/08 |
| WO | WO-2021224755 | A1 | * | 11/2021 | A42B 3/127 |
| WO | WO-2022107060 | A1 | * | 5/2022 | A42B 3/326 |

* cited by examiner

PROTECTIVE HELMET

CROSS REFERENCE TO RELATED APPLICATIONS

This application is a U.S. National Phase of PCT/EP2022/067881 filed Jun. 29, 2022, which claims priority to European Application No. 10 2021 116 755.8 filed Jun. 29, 2021, and European Application No. 10 2021 117 299.3 filed Jul. 5, 2021, all of which are incorporated herein in their entirety.

FIELD OF THE INVENTION

The invention relates to a protective helmet and in particular a motorcycle protective helmet.

BACKGROUND OF THE INVENTION

Protective helmets known as flip-up helmets in particular have both a chin part and a visor, which can both be respectively pivoted. If the chin part is in the lower position, it covers the chin portion of the protective helmet wearer. In this position of the chin part, the visor can, on the one hand, be moved to the closed position, in which the protective helmet is then completely closed, and, on the other hand, can be moved to the open position. In this open position, the visor exposes the sight opening and is pivoted to a position above the sight opening. This enables the rider to ventilate the inside region of the helmet and to get more fresh air.

The chin part can also be regularly pivoted to an upper position. If the visor is in the closed position prior to such pivoting, the visor is pivoted upwards with the chin part and thus maintains its position relative to the chin part. If the helmet wearer pivots the chin part from the upper position back to the lower position, the visor follows with the chin part and is likewise back in the same position as at the start.

If, on the other hand, the chin part is in the lower position and the visor is in the open position and if the chin part is then pivoted to the upper position from such a position, the visor either remains in its position relative to the helmet shell such that the chin part moves towards the visor or the visor moves further towards the open position to a lesser extent than the chin part. As a result, the chin part and visor move towards each other. Once the chin part has reached the upper position, the position of the chin part and visor is the same as it would be if the chin part were pivoted upwards with the visor closed. The reason for this is that the visor should not be moved upwards as far as desired, particularly for aerodynamic reasons. As the pivoting mechanism of the visor fixes it relative to the chin part, pivoting the chin part back to the lower position causes the visor to follow the chin part and then to be in the closed position. The disadvantage of this is that this does not correspond to the state of the visor before the chin part was pivoted from the lower position. Pivoting the chin part and pivoting it back thus leads to the visor being closed.

SUMMARY OF THE INVENTION

Based on this prior art, the object of the invention therefore involves further developing and improving the known protective helmet such that it provides an improved level of comfort in terms of the positioning of the visor and chin part during pivoting movements.

A key aspect of the invention is the concept that a coupling mechanism can be provided, which "remembers" the position of the visor in relation to the chin part before the chin part is pivoted. Even if the position of the visor relative to the chin part temporarily changes in the upper position of the chin part, the visor can remain in its earlier position or move back to its earlier position after the chin part has been pivoted back to the lower position. In this way, the protective helmet has a memory function in terms of the position of the visor during pivoting movements of the chin part.

The proposed protective helmet, which can in particular be a motorcycle protective helmet, has a helmet shell, a chin part for covering a chin portion of a protective helmet wearer, a coupling mechanism, by means of which the chin part is fastened to the helmet shell so as to be pivotable between a lower position and an upper position, and a visor, which visor, with the chin part in the lower position, by means of the coupling mechanism, can assume a respective pivoting position between a closed position for at least partially covering a field of view of the protective helmet wearer and an open position for freeing the field of view.

The helmet shell can in particular have an outer shell for distributing impact forces as well as an inner layer accommodated by the outer shell for damping impact forces. In addition to the outer shell and the inner layer, all other components of the protective helmet that are rigidly connected to the helmet shell are preferably also included here and below under the term "helmet shell". In addition to the visor, the protective helmet can also have a sun visor, which may also be pivotable, or another device to protect the eye area of the protective helmet wearer. In particular, the protective helmet can be a flip-up helmet. It is preferable that the protective helmet is substantially completely closed with the chin part in the lower position and the visor in the closed position. The visor preferably completely covers the field of view of the protective helmet wearer in the closed position.

It is possible that the chin part can assume any number of intermediate positions in addition to the lower position and the upper position. It is also possible that the visor can assume any number of intermediate positions between the closed position and the open position.

The proposed protective helmet is characterized in that the coupling mechanism is designed, upon pivoting of the chin part from the upper position to the lower position after the chin part has previously been pivoted from the lower position to the upper position, to cause the visor to occupy a pre-pivoting position differing from the closed position, which pre-pivoting position the visor occupied before the pivoting of the chin part from the lower position to the upper position. This pre-pivoting position can be any pivoting position of the visor except the closed position.

In the case of protective helmets from the prior art, it is often the case, as already described, that if the visor was in the closed position with the chin part in the lower position, then the visor is also in the closed position again after the chin part is pivoted to the upper position and then back to the lower position. This is because pivoting the chin part to the upper position and pivoting it back to the lower position regularly returns the visor to the closed position (in relation to the chin part), regardless of the previous pivoting position of the visor. In the case of the proposed protective helmet, this therefore applies to pivoting positions of the visor other than the closed position. However, this return to the previous position of the visor can also apply to the closed position of the visor in the case of the proposed protective helmet. This memory function for the closed position of the visor is therefore by no means excluded. It is simply not sufficient to provide such a memory function only for the closed position of the visor.

In other words, pivoting the chin part from the lower to the upper position and back again means that the visor either remains in the position that it had before the pivoting of the chin part, i.e. the pre-pivoting position, or is moved back to this earlier position. In other words, the visor can change its position relative to the chin part in the meantime, but is then returned to its earlier position.

One preferred embodiment of the protective helmet is characterized in that the coupling mechanism is designed, upon pivoting of the chin part from the lower position to the upper position with the visor in the open position, to move the chin part towards the visor in such a way that the visor is closer to the chin part in the upper position of the chin part. This can be achieved in particular by the visor either not following the pivoting movement of the chin part at all or only to a lesser extent.

Another preferred embodiment of the protective helmet is characterized in that, upon pivoting of the chin part from the lower position to the upper position with a visor in the closed position, the chin part maintains its position relative to the visor. If the visor is therefore in engagement with the chin part prior to pivoting or closes the front side of the protective helmet, then this is also the case after the chin part has been pivoted. It is preferably the case that, upon pivoting of the chin part from the lower position to the upper position with a visor in the closed position, the visor is carried along by the chin part and alternatively or additionally by the coupling mechanism.

According to one preferred embodiment of the protective helmet, it is provided that the coupling mechanism has a latching device, which is pivotably coupled to the helmet shell. In other words, although there is a direct or indirect mechanical connection between the latching device and the helmet shell, the latching device can always be pivoted relative to the helmet shell. Furthermore, it is preferable that the visor is pivotably coupled to the latching device for changing the pivoting position. This coupling between the visor and the latching device, which coupling enables the change of the pivoting position, can also be direct or indirect. Furthermore, it is preferable that the pivoting position of the visor is defined by a relative pivoting of the visor to the latching device and a relative pivoting of the latching device to the helmet shell. This means that, at least for some pivoting positions of the visor, no position of the latching device in relation to the helmet shell is clearly defined. Rather, the latching device has a corresponding degree of freedom with regard to its pivoting position. It can further be the case that the visor can form a respective latching connection with the latching device in a plurality of positions relative to the latching device. The visor is then preferably held in the respective relative position by the latching connection.

According to another preferred embodiment of the proposed protective helmet, it is provided that the latching device is pivotably mounted relative to the chin part. In particular, it can be the case that the latching device is designed to take along the visor when the latching device is pivoted relative to the helmet shell, preferably by means of the respective latching connection. This makes it possible to pivot the visor by actuating the latching device. However, the latching device is not regularly actuated in this way through direct manual intervention of the protective helmet wearer, but rather through the intervention of another component of the protective helmet. This other component can then for its part be directly or indirectly actuated by the protective helmet wearer.

This additional degree of freedom of the latching device can also be optionally cancelled. In this way, the described memory function can be temporarily cancelled. One preferred embodiment of the proposed protective helmet is characterized in that the coupling mechanism has a releasable locking device for rigid coupling of the latching device with the chin part. If the latching device is rigidly coupled with the chin part, a closed position of the visor in the upper position of the chin part also leads to a closed position of the visor when the chin part is pivoted back to the lower position.

In principle, the mechanical interaction between the chin part and the latching device can take any form. According to one preferred embodiment of the proposed protective helmet, it is provided that the coupling mechanism has a latch carrier, which is preferably rigidly connected to the chin part. In particular, it can be the case that the latch carrier engages with the latching device in the lower position of the chin part in such a way that the latching device is fixed in a closed position of the latching device. This means that the chin part forces the latching device into a specific position by means of the latch carrier, i.e. the closed position, when the chin part is in the lower position.

According to another preferred embodiment of the proposed protective helmet, it is provided that the coupling mechanism is designed to cause the visor to change its pivoting position by changing its position relative to the latching device in response to actuation of the visor with the latching device fixed by the latch carrier. In other words, fixing the latching device does not prevent the visor from pivoting. However, this fixing means that the pivoting of the visor is not accompanied by a corresponding pivoting movement of the latching device, but rather results in a relative movement between the visor and the latching device.

Whilst the latching device is therefore preferably fixed in a position when the chin part is in the lower position, mobility of the latching device is preferred when the chin part is in the upper position. This degree of freedom enables the coupling mechanism to "remember" the previous position of the visor according to the relative position of the visor and latching device. Accordingly, one preferred embodiment of the proposed protective helmet is characterized in that in the upper position of the chin part, a pivoting movement of the latching device around the helmet shell is unblocked in at least one direction. This preferably applies to all positions of the latching device. Unblocked in at least one direction means that the latching device can be pivoted in at least one pivoting direction without being directly blocked.

In principle, the mechanical interaction between the chin part and the visor can also take any form. Another preferred embodiment of the proposed protective helmet is characterized in that the coupling mechanism has a visor carrier, which is preferably rigidly connected to the chin part. In particular, it can be the case that the visor carrier is in engagement with the visor when the chin part is in the lower position and the visor is in the closed position.

According to a preferred embodiment of the proposed protective helmet, it is provided that, upon pivoting of the chin part from the lower position to the upper position with the visor in the closed position, the visor is carried along by the visor carrier. It is further preferable that by the visor being carried along by the visor carrier, the visor carries along the latching device. Not only does the visor therefore follow the movement of the chin part, but also the latching device follows the movement of the chin part indirectly by means of the visor.

Another preferred embodiment of the proposed protective helmet is characterized in that the visor carrier and/or the latch carrier is arranged in a side region of the protective helmet. The coupling mechanism is preferably arranged on both sides substantially opposite each other in a respective side region of the protective helmet.

According to another preferred embodiment of the proposed protective helmet, it is provided that in the upper position of the chin part, a pivoting movement of the visor in the direction of the closed position is limited by the visor carrier and further in the direction of the open position by an upper stop of the coupling mechanism rigidly connected to the helmet shell. In this way, the visor is fixed in the upper position of the chin part. The position of the visor when the chin part is in the lower position is then stored by the position of the visor relative to the latching device.

In principle, the various pivoting movements can be performed around different axes. One preferred embodiment of the proposed protective helmet is characterized in that the visor and the chin part can be pivoted about a common pivot axis. It is further preferable that the latching device can be pivoted about the common pivot axis.

Another preferred embodiment of the proposed protective helmet is characterized in that the visor carrier has a visor projection, which during a pivoting movement of the chin part, performs a pivoting movement in a pivot plane on a first radius about the pivot axis, which first radius is different from a second radius about the pivot axis, on which second radius the latching device is arranged in the pivot plane about the pivot axis. The pivot plane is a plane defined by the pivot axis. By virtue of the fact that the visor projection is arranged radially offset to the latching device within the pivot plane, the chin part and the latching device can be positioned substantially freely in relation to one other.

Figure 2:
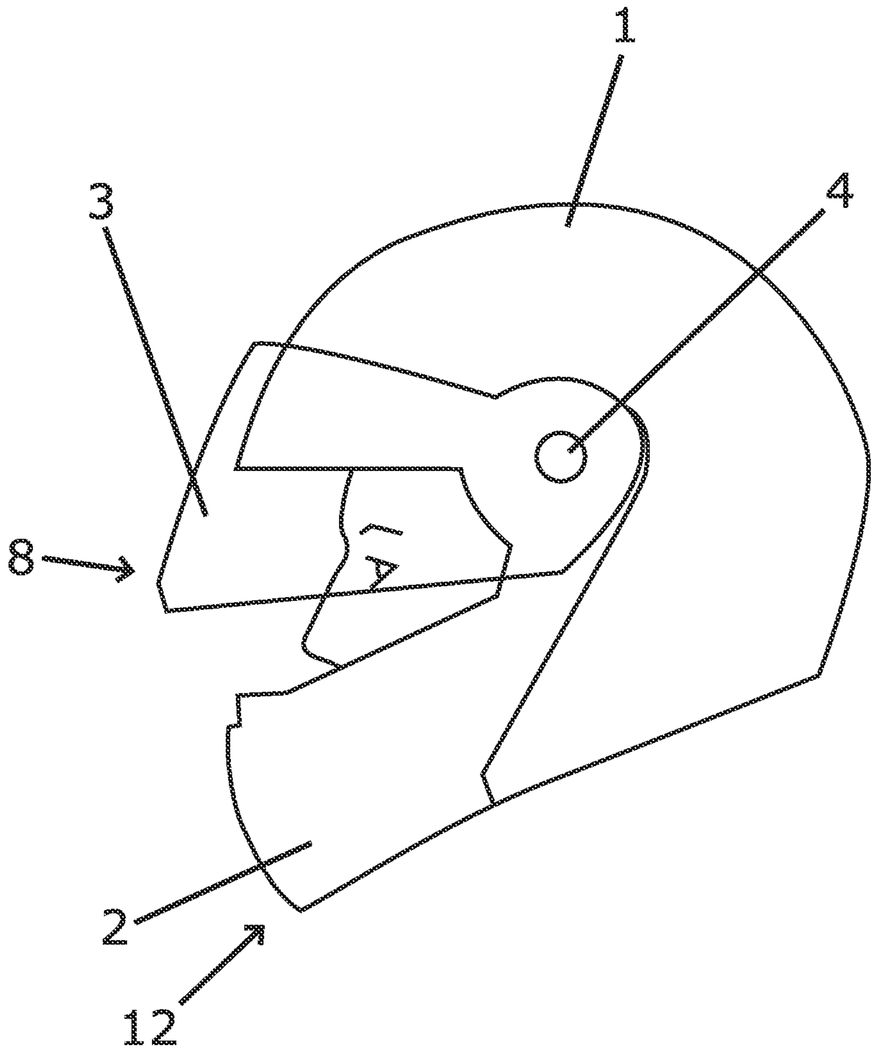
Figure 3:
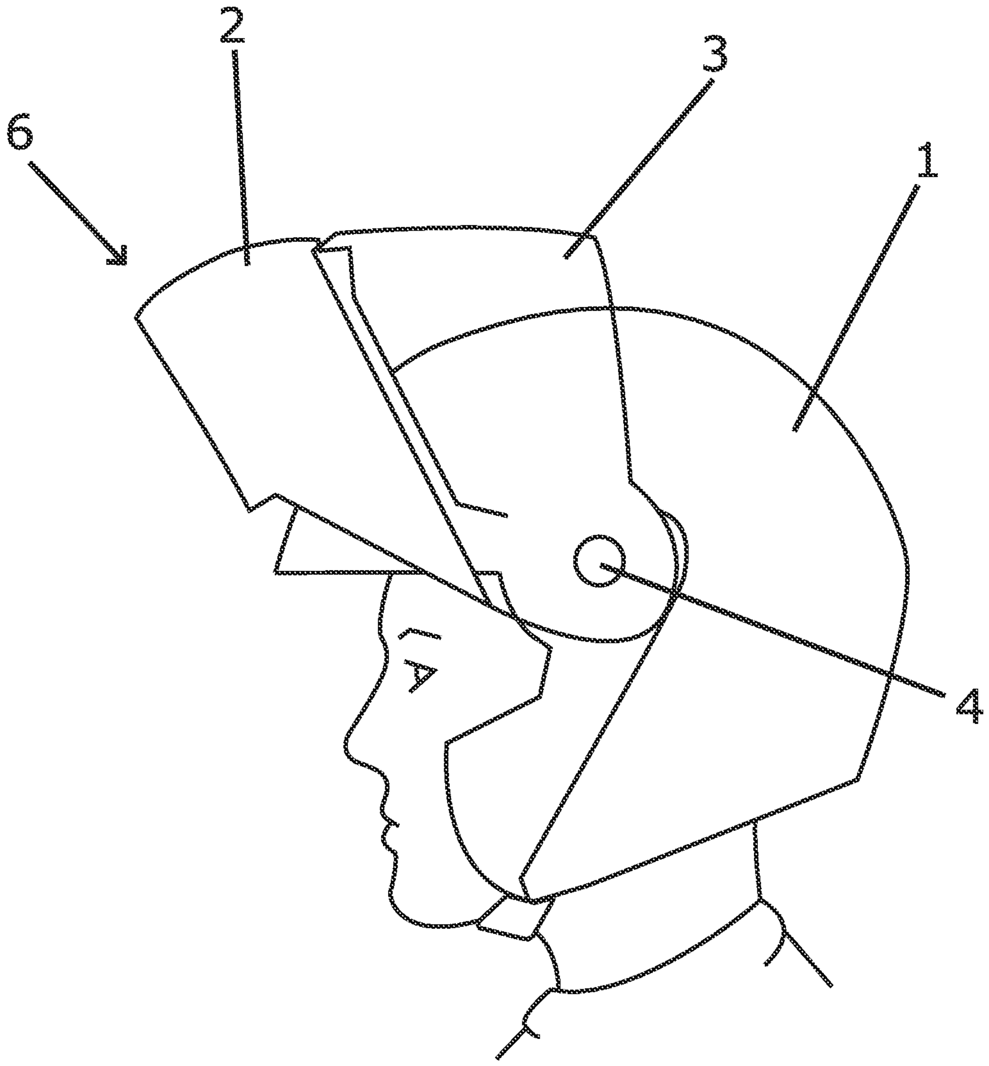
Figure 4:
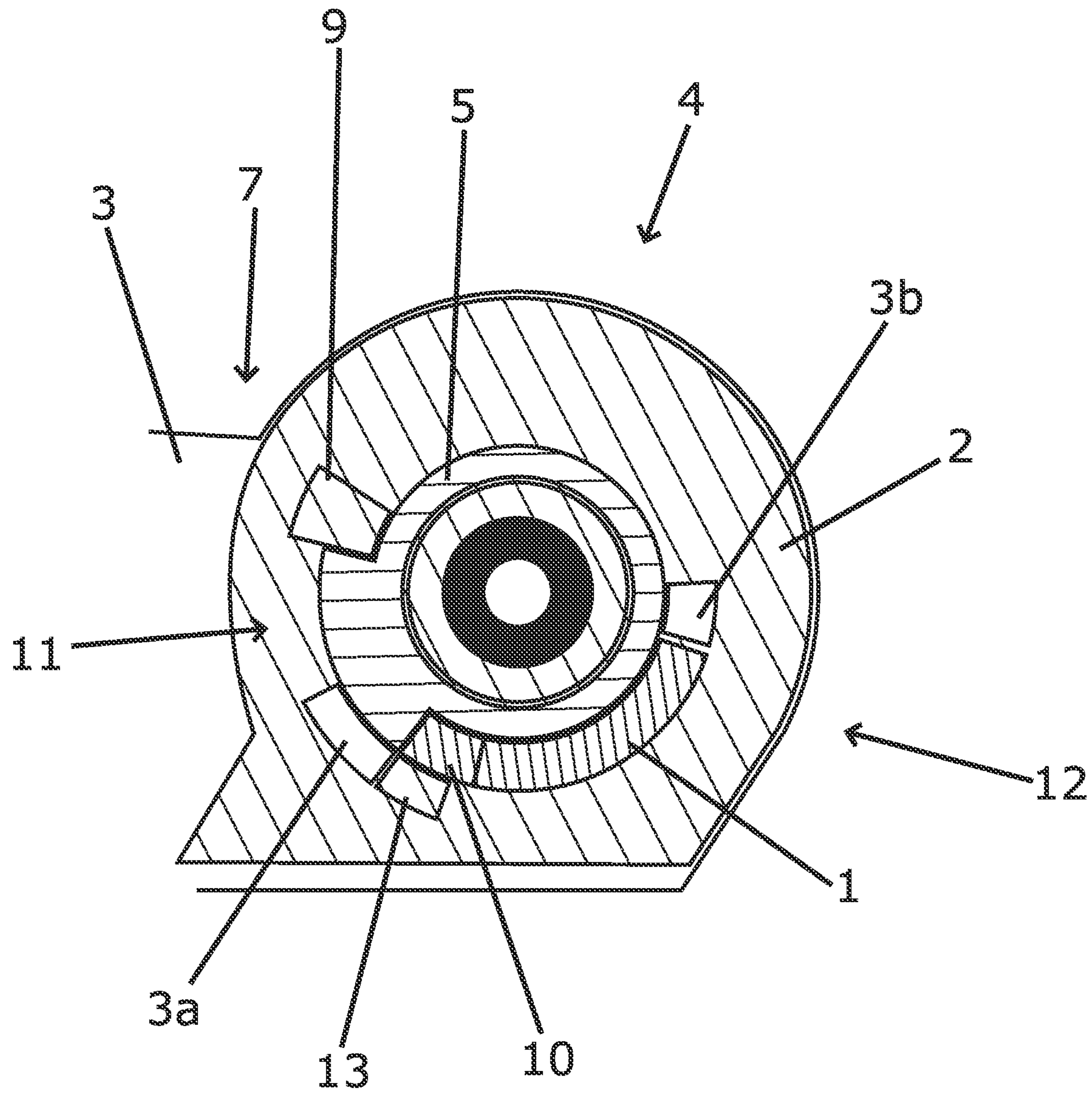
Figure 5:
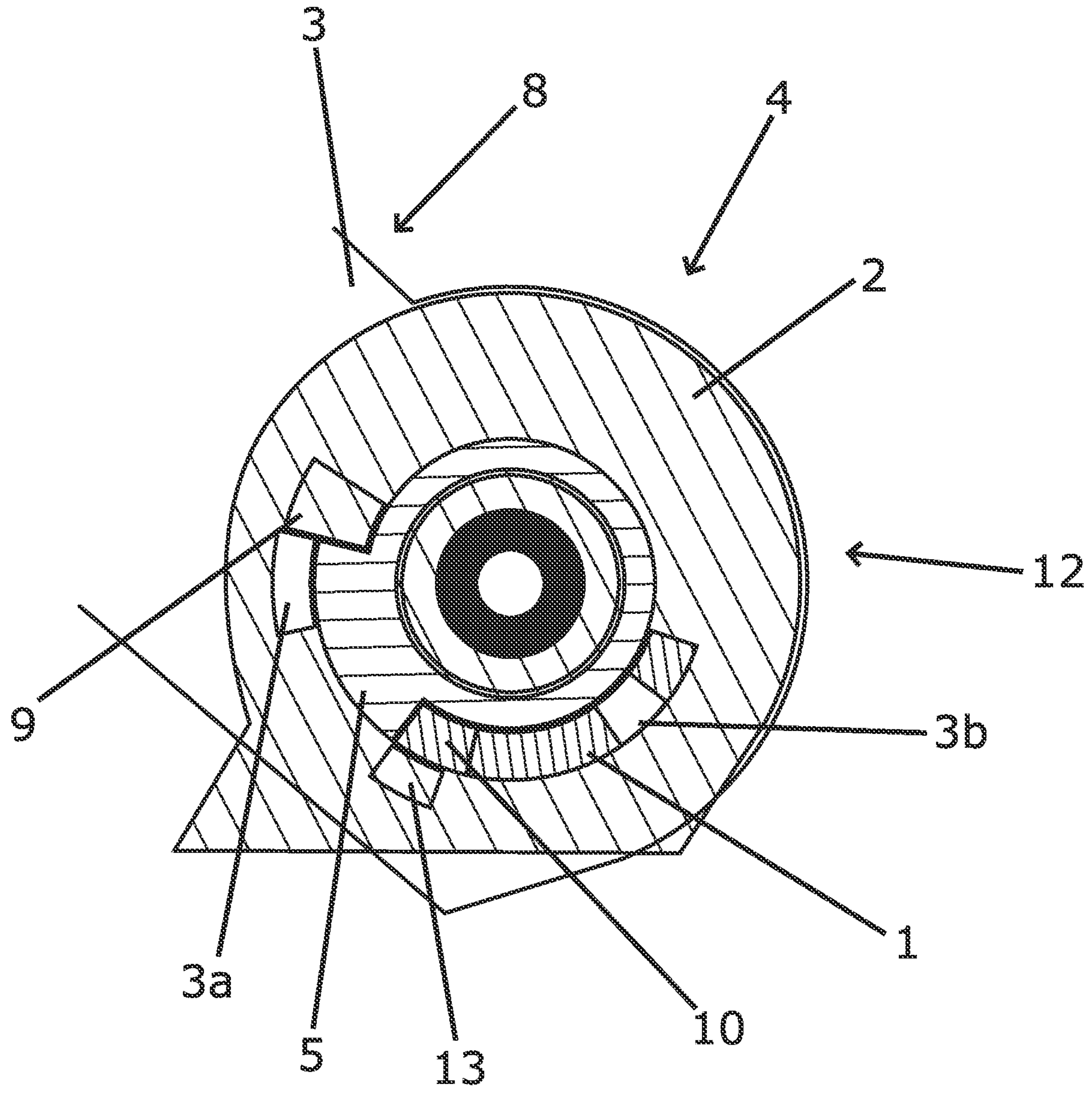
Figure 6:
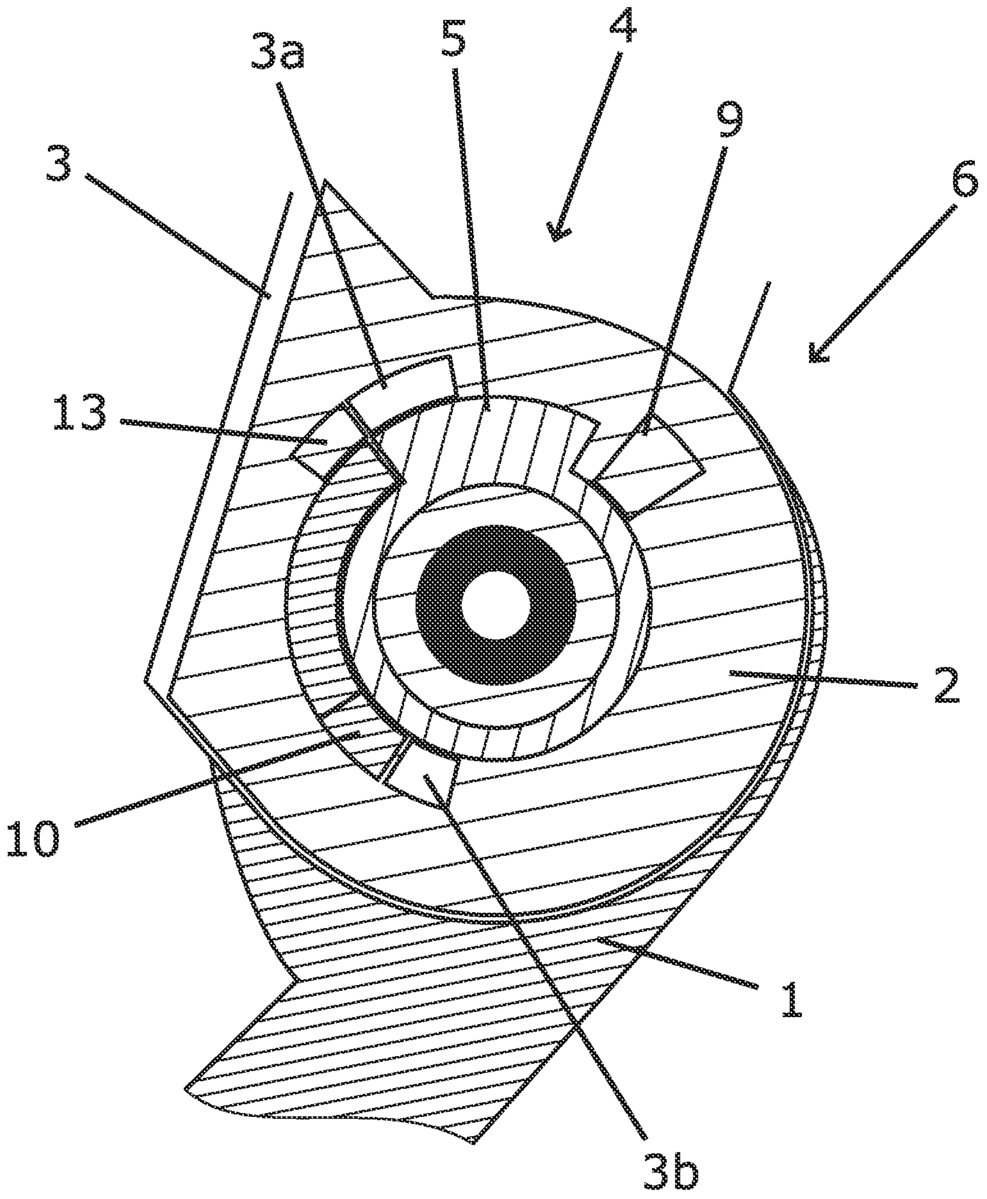
Figure 7:
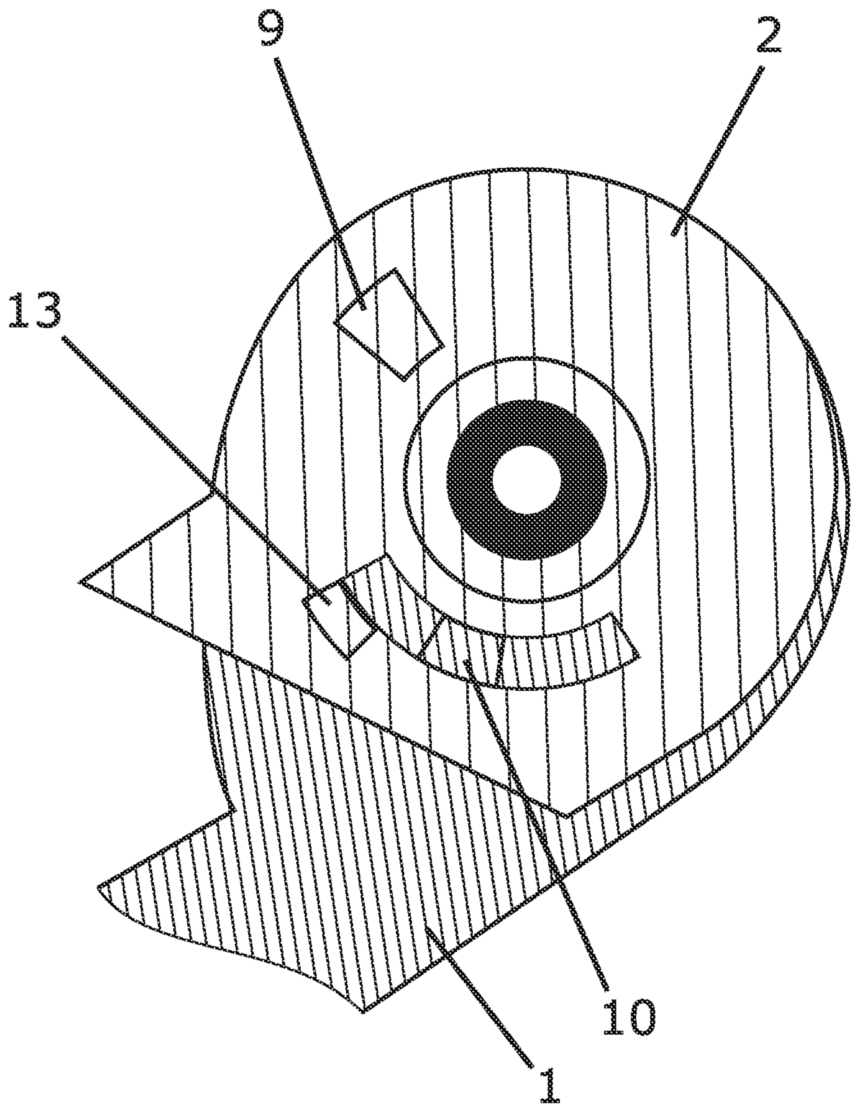
Figure 8:
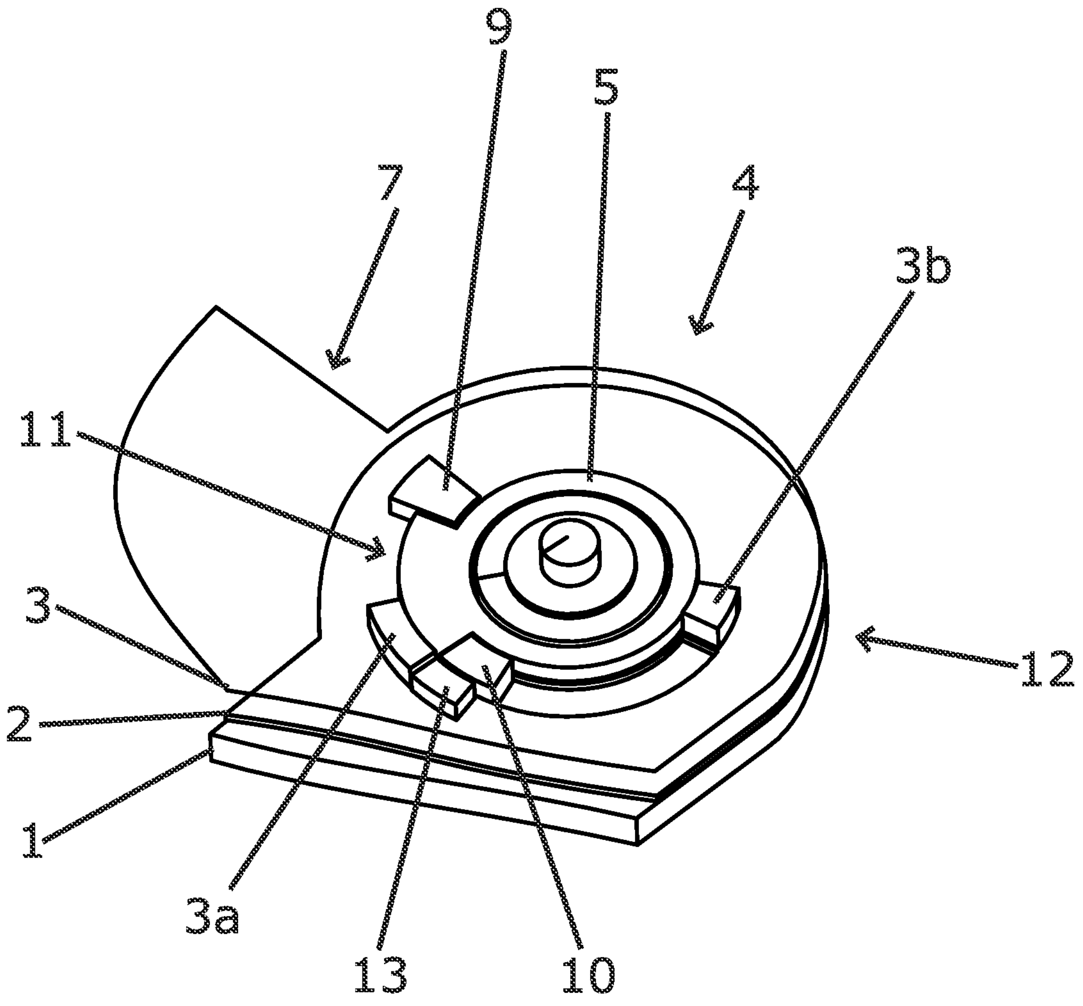
Figure 9:
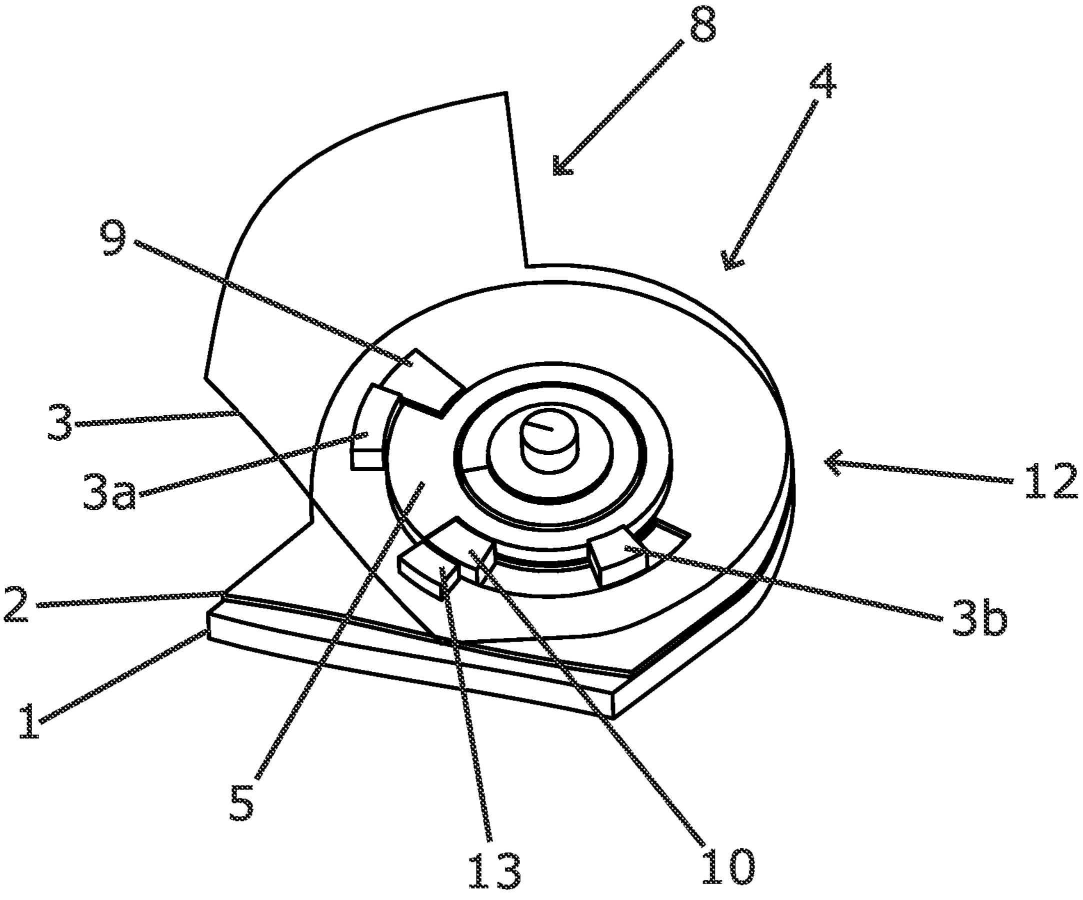
Figure 10:
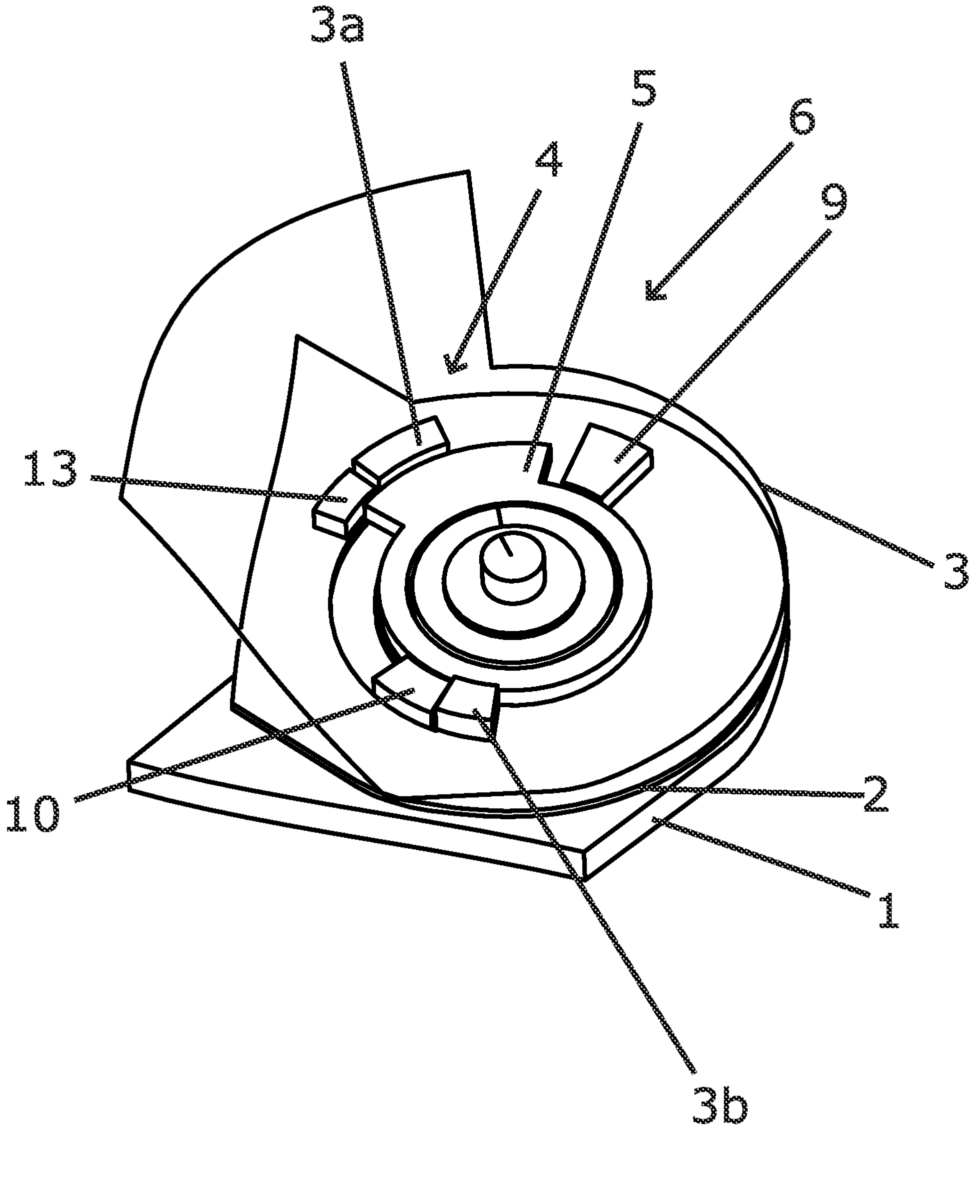
Figure 11:
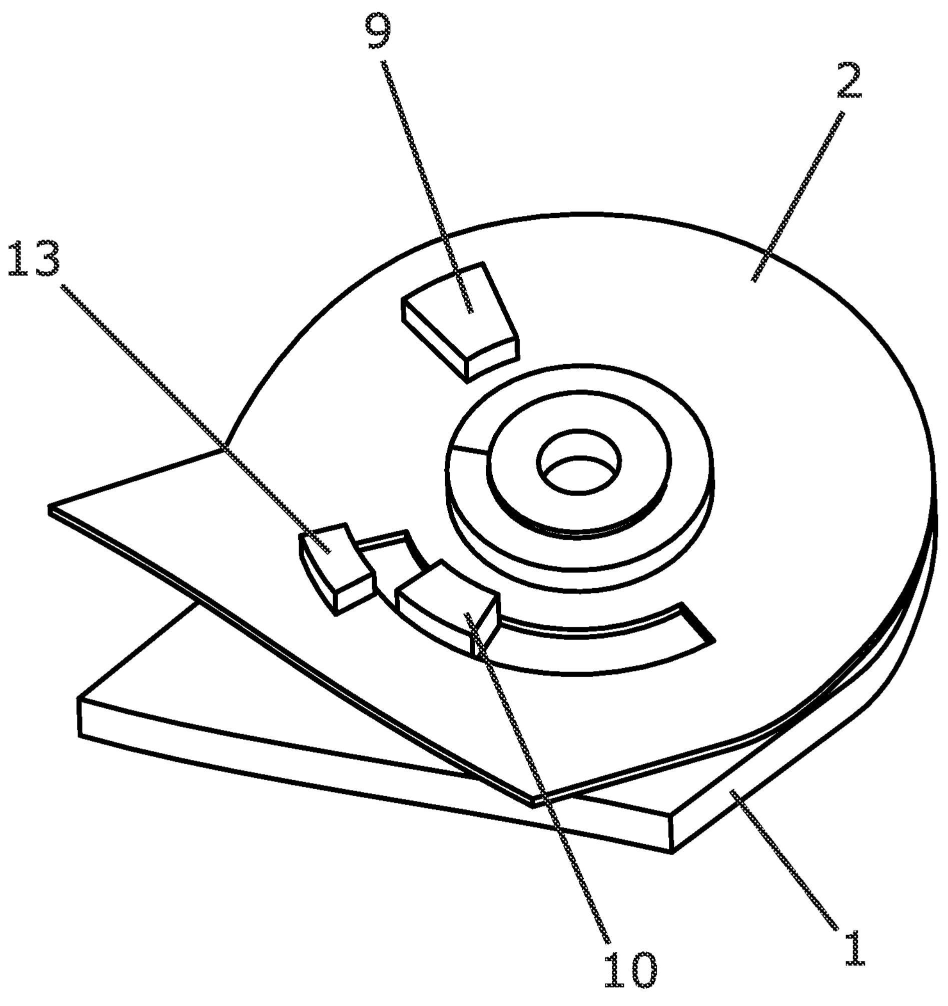

Further advantageous and preferred embodiments will result from the following description with reference to the figures. In the drawing, which only shows exemplary embodiments:

FIG. 1 shows a schematic side view of a first exemplary embodiment of a proposed protective helmet with the chin part in the lower position and the visor in the closed position, FIG. 2 shows a schematic side view of the protective helmet shown in FIG. 1 with the chin part in the lower position and the visor in an intermediate position between the closed position and the open position, FIG. 3 shows a schematic side view of the protective helmet shown in FIG. 1 with the chin part in the upper position and the visor relative to the chin part in the closed position, FIG. 4 shows a schematic plan view of the coupling mechanism of the protective helmet shown in FIG. 1 with the chin part in the lower position and the visor in the closed position, FIG. 5 shows a schematic plan view of the coupling mechanism of the protective helmet shown in FIG. 1 with the chin part in the lower position and the visor in the open position, FIG. 6 shows a schematic plan view of the coupling mechanism of the protective helmet shown in FIG. 1 with the chin part in the upper position and the visor in a compact position, FIG. 7 shows a schematic top view of the mounting of the chin part on the helmet shell in the coupling mechanism of the protective helmet shown in FIG. 1, FIG. 8 shows a schematic perspective view of the coupling mechanism of a second exemplary embodiment of a proposed protective helmet with the chin part and the visor in a respective position according to FIG. 4, FIG. 9 shows a schematic perspective view of the coupling mechanism shown in FIG. 8 with the chin part and the visor in a respective position according to FIG. 5, FIG. 10 shows a schematic perspective view of the coupling mechanism shown in FIG. 8 with the chin part and the visor in a respective position according to FIG. 6 and FIG. 11 shows a schematic perspective view of the mounting of the chin part on the helmet shell in the coupling mechanism shown in FIG. 8 in respective positions according to FIG. 7.

DETAILED DESCRIPTION OF THE DRAWINGS

The proposed protective helmet shown in FIG. 1 according to the first exemplary embodiment is a motorcycle protective helmet and specifically a flip-up helmet. It has a helmet shell 1 as well as a chin part 2, a visor 3 and a coupling mechanism 4. The chin part 2 and the visor 3 can be pivoted by means of the coupling mechanism 4, wherein various positions of the chin part 2 and of the visor 3 are respectively shown in FIGS. 1, 2 and 3.

In FIGS. 1 and 2, the chin part 2 is in its lower position 12, whereas the chin part 2 in FIG. 3 is in its upper position 6. In FIG. 1, the visor 3 is in its closed position 7. In FIG. 2, the visor 3 is in an intermediate position between the closed position 7 and the open position. This intermediate position of the visor 3 corresponds here to the pre-pivoting position 8 by way of example. The pivoting position of the visor 3 in FIG. 3 is a compact position, which is even beyond the open position.

If now, based on the situation in FIG. 2, the chin part 2 is pivoted to the upper position 6 according to FIG. 3, the visor 3 correspondingly assumes the compact position shown in FIG. 3. When the chin part 2 is pivoted back to the lower position 12, the visor 3 also returns to the intermediate position according to FIG. 3, specifically therefore to the pre-pivoting position 8. The pre-pivoting position 8 is therefore the pivoting position that the visor 3 occupied before the chin part 2 was pivoted.

This "remembering" of the pre-pivoting position 8 and the return of the visor 3 to it is enabled by the coupling mechanism 4 shown in detail in FIGS. 4 to 7.

FIG. 4 shows the coupling mechanism 4 in the state of the protective helmet according to FIG. 1. The helmet shell 1, the chin part 2 and the visor 3 are arranged one above the other in the direction of the drawing plane—in this order. In FIG. 4, only a component rigidly coupled to the helmet shell 1 can be seen through an arcuate opening, which is also regarded as a component of the helmet shell 1 in accordance with the above findings. It should be noted that only a small part of these components is shown here schematically and the connection to the components is not shown. For the visor 3, a first visor projection 3*a* and a second visor projection 3*b* are shown separately for clarity. These are part of the visor 3 and rigidly coupled to the visor 3.

The visor 3 can form a respective latching connection with the latching device 5 by latching points (not shown here). These latching points are distributed along the latching device 5 in such a way that such a latching connection is produced in different pivoting positions of the visor 3 relative to the latching device 5.

The coupling mechanism 4 has a latch carrier 9 rigidly connected to the chin part 2, which in the lower position 12 of the chin part 2 together with an upper stop 10 of the coupling mechanism 4, which upper stop 10 is rigidly coupled with the helmet shell 1, fixes the latching device 5 in the position shown. The position of the latching device 5 is referred to here as the closed position 11.

Fixing the latching device 5 in the closed position 11 leads to an actuation of the visor 3 in the direction of the open position causing a relative movement between the visor 3 and the latching device 5. The existing latching connection between the visor 3 and the latching device 5 is therefore released and a new latching connection is created in a different position.

The described actuation of the visor 3 leads, by way of example, to a position of the visor 3 as shown in FIG. 5, which can also be referred to as a pre-pivoting position 8. It should be noted that this pre-pivoting position 8 is different from the pre-pivoting position 8 shown in FIG. 2 as the visor 3 according to FIG. 5 is further open than in FIG. 2. However, this difference is insignificant in terms of how the coupling mechanism 4 functions. It can be seen that the position of the latching device 5 has not changed as a result of the actuation of the visor 3.

In turn, FIG. 6 shows a state of the coupling mechanism 4 that is achieved when, starting from the state shown in FIG. 4, the chin part 2 is pivoted from the lower position 12 to the upper position 6. On the one hand, this pivoting movement releases the latching device 5 because the latch carrier 9 disengages from the latching device 5. On the other hand, a visor carrier 13, which is also rigidly coupled with the chin part 2 and formed as a visor projection here, engages in the visor 3 and more precisely in the first visor projection **3*a* and carries the visor 3 along in this way. The latching device 5 is also carried along during this pivoting movement as a result of the latching connection between the visor 3 and the latching device 5 without the latching connection between the visor 3 and latching device 5 being released. As a result, the visor 3 and the chin part 2 are positioned as shown in FIG. 3**.

It can be seen that the relative position between the visor 3 and the latching device 5 is maintained in this way. At the same time, the latching device 5 always has play in relation to a pivoting movement. In particular, no carrier engages directly with the latching device 5. In contrast, the visor 3 is fixed in its position, as it engages with the visor carrier 13 in the one pivoting direction and with the upper stop 10 in the other pivoting direction. If the chin part 2 is then moved back to the lower position 12, the state shown in FIG. 4 is restored.

This also shows what happens when, starting from the situation in FIG. 5, the chin part 2 is pivoted from the lower position 12 to the upper position 6. Despite the different pivoting position of the visor 3 compared to FIG. 4 prior to the pivoting movement—which pivoting position is again to be referred to here as a pre-pivoting position 8—the visor 3 and chin part 2 also assume a position as in FIG. 3. However, despite the identical position of the visor 3, the configuration of the coupling mechanism 4 is different from that shown in FIG. 6, as the relative position between the visor 3 and the latching device 5 according to FIG. 5 is maintained by the latching connection. With reference to the illustration in FIG. 6, the latching device 5 is simply pivoted anticlockwise, which is in turn enabled by the existing degree of freedom for the latching device 5. This means that when the chin part 2 is pivoted back to the lower position 12, the visor 3 can return back to its previous pivoting position, i.e. the pre-pivoting position 8.

For a better understanding, the coupling mechanism 4 is shown without visor 3 and without latching device 5 in FIG. 7.

FIGS. 8 to 11 show the coupling mechanism 4 or parts of the coupling mechanism 4 of a second exemplary embodiment of the proposed protective helmet in a schematic perspective view.

FIGS. 8 to 11 substantially correspond to FIGS. 4 to 7 in terms of the components shown and their basic positions. Differences exist only in the special measurements, angles and dimensions and similar details such that the above observations on FIGS. 4 to 7 and the components mentioned therein also apply substantially to FIGS. 8 to 11 and the perspective view of FIGS. 8 to 11 supplements that of FIGS. 4 to 7.

The invention claimed is:

1. Protective helmet having a helmet shell, a chin part configured to cover a chin portion of a protective helmet wearer, a coupling mechanism, by which the chin part is pivotably mounted to the helmet shell and is movable between a lower position and an upper position, and a visor, which, when the chin part is in the lower position, is pivotably mounted by the coupling mechanism and is movable to a respective pivoting position between a closed position, in which the visor at least partially covers a field of view of the protective helmet wearer, and an open position, in which the visor exposes the field of view, wherein the coupling mechanism is configured such that, when the chin part is pivoted from the lower position to the upper position and subsequently returned to the lower position, the visor is returned to a pre-pivoting position, which pre-pivoting position is different from the closed position and corresponds to the respective pivoting position occupied by the visor prior to pivoting the chin part from the lower position to the upper position.

2. Protective helmet according to claim 1, wherein the coupling mechanism is configured such that, when the chin part is pivoted from the lower position to the upper position with the visor in the open position, the chin part is moved towards the visor in such a way that, in the upper position of the chin part, the visor is closer to the chin part than in the lower position.

3. Protective helmet according to claim 1, wherein, when the chin part is pivoted from the lower position to the upper position with the visor in the closed position, the position of the chin part relative to the visor is maintained.

4. Protective helmet according to claim 1, wherein the coupling mechanism has a latching device, which is pivotably coupled to the helmet shell, and wherein the visor is pivotably coupled to the latching device for changing the respective pivoting position.

5. Protective helmet according to claim 4, wherein the latching device is pivotably mounted relative to the chin part.

6. Protective helmet according to claim 4, wherein the coupling mechanism has a releasable locking device configured to rigidly couple the latching device to the chin part.

7. Protective helmet according to claim 1, wherein the coupling mechanism has a latch carrier, rigidly connected to the chin part.

8. Protective helmet according to claim 7, wherein the coupling mechanism is configured such that, when the latching device is fixed by the latch carrier, the visor is movable to change its respective pivoting position relative to the latching device in response to actuation of the visor.

9. Protective helmet according to claim 7, wherein, in the upper position of the chin part, the latching device is unblocked and is pivotable around the helmet shell in at least one direction.

10. Protective helmet according to claim 1, wherein the coupling mechanism has a visor carrier rigidly connected to the chin part.

11. Protective helmet according to claim 10, wherein, when the chin part is pivoted from the lower position to the upper position with the visor in the closed position, the visor is carried along by the visor carrier.

12. Protective helmet according to claim 10, wherein the visor carrier and/or the latch carrier is arranged in a side region of the protective helmet, and wherein the coupling mechanism is arranged on both sides of the protective helmet in substantially opposite side regions.

13. Protective helmet according to claim 11, wherein, in the upper position of the chin part, a pivoting movement of the visor toward the closed position is limited by the visor carrier, and a further pivoting movement of the visor toward the open position is limited by an upper stop of the coupling mechanism rigidly connected to the helmet shell.

14. Protective helmet according to claim 1, wherein the visor and the chin part are pivotable about a common pivot axis, and wherein the latching device is pivotable about the common pivot axis.

15. Protective helmet according to claim 14, wherein the visor carrier has a visor projection, which, during a pivoting movement of the chin part, performs a pivoting movement in a pivot plane on a first radius about the pivot axis, the first radius being different from a second radius about the pivot axis, on which second radius the latching device is arranged in the pivot plane about the pivot axis.

16. Protective helmet according to claim 1, wherein the protective helmet is a motorcycle protective helmet.

17. Protective helmet according to claim 3, wherein when the chin part is pivoted from the lower position to the upper position with the visor in the closed position, the visor is carried along by the chin part and/or by the coupling mechanism during such pivoting.

18. Protective helmet according to claim 4, wherein the visor is configured to form a latching connection with the latching device in a plurality of positions relative to the latching device.

19. Protective helmet according to claim 5, wherein the latching device is configured to carry along the visor when the latching device is pivoted relative to the helmet shell via the respective latching connection.

20. Protective helmet according to claim 7, wherein the latch carrier is configured to engage with the latching device in the lower position of the chin part in such a way that the latching device is fixed in a closed position of the latching device.

21. Protective helmet according to claim 10, wherein the visor carrier is configured to engage with the visor when the chin part is in the lower position and the visor is in the closed position.

22. Protective helmet according to claim 11 wherein the visor, when carried along by the visor carrier, carries along the latching device.

* * * * *